(12) United States Patent
Rojas et al.

(10) Patent No.: US 8,647,686 B1
(45) Date of Patent: Feb. 11, 2014

(54) INSECT DIET FORMULATIONS AND METHODS FOR REARING INSECTS

(75) Inventors: Maria G. Rojas, Greenville, MS (US); Juan A. Morales Ramos, Greenville, MS (US)

(73) Assignee: The United States of America, as represented by the Secretary of Agriculture, Washington, DC (US)

(*) Notice: Subject to any disclaimer, the term of this patent is extended or adjusted under 35 U.S.C. 154(b) by 849 days.

(21) Appl. No.: 12/229,920

(22) Filed: Aug. 27, 2008

Related U.S. Application Data

(60) Provisional application No. 60/969,003, filed on Aug. 30, 2007.

(51) Int. Cl.
*A23K 1/18* (2006.01)
*A23L 1/30* (2006.01)
*A23K 1/17* (2006.01)

(52) U.S. Cl.
USPC .......... 426/2; 426/72; 426/74; 426/658; 426/442

(58) Field of Classification Search
CPC ........................................... A23K 1/18
USPC .............. 426/20, 2, 74, 72, 658; 424/442
See application file for complete search history.

(56) References Cited

U.S. PATENT DOCUMENTS

| | | | | | |
|---|---|---|---|---|---|
| 4,670,268 | A | * | 6/1987 | Mahmoud | 426/72 |
| 5,834,177 | A | * | 11/1998 | Cohen | 435/1.1 |
| 7,789,039 | B2 | * | 9/2010 | Hance et al. | 119/6.5 |
| 2004/0057977 | A1 | * | 3/2004 | Gardner et al. | 424/410 |
| 2008/0260908 | A1 | * | 10/2008 | Mutilangi et al. | 426/72 |

* cited by examiner

*Primary Examiner* — Rena Dye
*Assistant Examiner* — Lela S Williams
(74) *Attorney, Agent, or Firm* — John D. Fado; David L. Marks

(57) ABSTRACT

A composition suitable for the preparation of insect diet formulations, containing proteins, carbohydrates, vitamins, salts, and lambda carrageenan; the composition contains maltodextrin and no agar. An insect diet formulation, containing the composition described herein and water (room temperature). A method for rearing insects from eggs, involving providing the insect diet formulation described herein and culturing the insects with the insect diet formulation.

6 Claims, 5 Drawing Sheets

INSECT DIET FORMULATIONS AND METHODS FOR REARING INSECTS

REFERENCE TO RELATED APPLICATION

This application claims the benefit of U.S. Provisional Application No. 60/969,003, filed 30 Aug. 2007, which is incorporated herein by reference in its entirety.

BACKGROUND OF THE INVENTION

The present invention relates to a composition suitable for the preparation of insect diet formulations, containing proteins, carbohydrates, vitamins, salts, and lambda carrageenan; the composition contains maltodextrin and no agar. In addition, the present invention relates to an insect diet formulation, containing the composition described herein and water (room temperature). Furthermore, the present invention relates to a method for rearing insects from eggs, involving providing the insect diet formulation described herein and culturing the insects with the insect diet formulation.

The present state of the art in producing solid artificial diets for insects and mites depends on the use of agar which must be mixed at high temperatures (90-95° C.). Agar has been extensively used in solid artificial diet formulations due to the lack of other alternatives. Although agar based diets are reliable, diet preparations using agar are complicated by the high temperature required to suspend it in water and to maintain its liquid state (55-60° C.) and to prevent solidification. Mixing critical nutrients (e.g., vitamins) into an agar based diet formulation requires very precise timing prior to the threshold of diet solidification in order to prevent the thermal breakdown of these critical nutrients. If this is not done correctly some nutrients may lose activity resulting in the compromised quality of the insects reared on these diets.

There thus remains a need in the art for an effective insect diet formulation that does not require high temperatures during the mixing process and for a method for culturing insects from the egg stage to adult. The present invention described below provides an insect diet formulation, completely devoid of agar, which enables rearing of many different species of insects which is different from prior art media which required the use of agar and high temperatures for mixing.

SUMMARY OF THE INVENTION

In accordance with the present invention, there is provided a composition suitable for the preparation of insect diet formulations, containing proteins, carbohydrates, vitamins, salts, and lambda carrageenan; the composition contains maltodextrin and no agar. Also in accordance with the present invention, there is provided an insect diet formulation, containing the composition described herein and water (room temperature). Additionally in accordance with the present invention, there is provided a method for rearing insects from eggs, involving providing the insect diet formulation described herein and culturing the insects with the insect diet formulation.

DETAILED DESCRIPTION OF THE INVENTION

Figure 1:
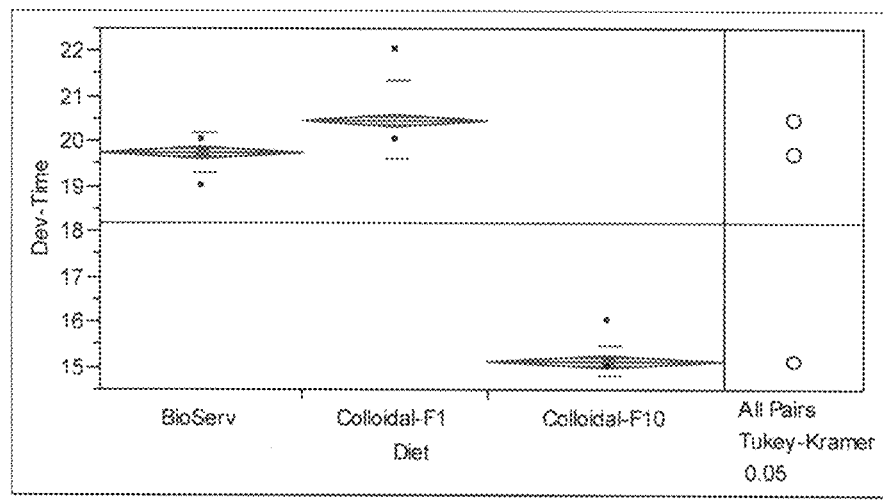
FIG. 1 shows analysis of variance and mean comparison of development time in days among $T.$ $ni$ reared on colloidal diet for one and 10 generations and in the BioSery diet. Rhombs middle line represents means, rhomb height represents confidence intervals, rhomb width represent number of observations and points represent observation values. Circles represent results of the Tuke-Kramer HSD test, overlapping circles correspond to means that are not significantly different.

The present invention concerns a composition suitable for the preparation of insect diet formulations, containing proteins, carbohydrates (e.g., starch, cellulose, sugars), vitamins, salts, and lambda carrageenan; the composition contains maltodextrin and contains no agar. In addition, the present invention concerns an insect diet formulation, containing the composition described herein and water (room temperature); the formulation contains no agar and is prepared without heating (at room temperature). Furthermore, the present invention concerns a method for rearing insects from eggs, involving providing the insect diet formulation described herein and culturing the insects with the insect diet formulation.

The insect diet formulation differs from current formulations in part by the use of less water. For example, current formulations need between 75% and 85% water (U.S. Patent Application 20040228947) while our insect diet formulation requires only about 53% water for solid diets. Furthermore, unlike current formulations, no heat is required in the preparation of the insect diet formulation and no water retaining agents are required (which reduces the content of compounds that are not related to insect nutrition thus allowing for the incorporation of more nutrients, especially protein, to end up with a more balanced diet).

Current insect diet formulations using kappa carrageenan require about 70° C. heat and a calcium salt in order to form a stable gel (Spencer, N. R., et al., Ent. Exp. & appl., 20: 39-42 (1976)). Other diets using kappa carrageenan (U.S. Patent Application 20040228947) require the addition of vermiculite (7-12%) as a gelling agent. These additives can become toxic for some insect species, thus reducing the number of insect species that can be reared using these formulations. Our colloid insect diet formulation does not require a gelling agent because it does not gel. It uses a stabilizing agent (maltodextrin) that is a non-toxic complex carbohydrate. In addition, our colloidal diet ingredients (including the lambda carrageenan) can be mixed at room temperature (about 20°-about 30° C. (e.g., 20°-30° C.)) whereas current formulations (U.S. Patent Application 20040228947) require the addition of boiling water.

Lambda carrageenan has not been used for arthropod diets since this carrageenan will not form a stable gel. Lambda carrageenan in our diet is used as a hardening agent combined with starch and cellulose. The consistency of the resulting semi solid diet (when 60-69% water is used) is similar to play dough or bread dough. The mixture is stabilized by the use of maltodextrin; addition of salts (e.g., calcium, and sodium) is not required. In addition to being a good diet for lepidopterous, coleopteran and other chewing insects, the colloid properties of this diet make it suitable for rearing arthropods that have external digestion such as mites, predatory sting bugs, lace wings, and clerid beetles. This property gives the colloid formulations a unique degree of flexibility that is not match by any existing diet formulation.

An important aspect of this colloid diet formulation is the simplicity of the mixing process and the flexibility of the final diet consistency, which allows for multiple possibilities for mechanization of the dispensing process. Eliminating the need for heat during the mixing process and the need for high temperature control during the dispensing process can simplify the mechanization of these two processes. In addition, the use of colloids in an insect diet will allow for new applications of solid diets for sucking insects and arthropods with external digestion. Our colloid formulations can improve digestion during external feeding, thus increasing the amount of nutrients that can be delivered in the formulation, especially protein. Liquid diets have been used to rear heteropterans, homopterans, and mites with poor results. The advantage of a solid diet formulation is the simplicity of its mixing and dispensing, which allows for mechanization and mass production. Our colloidal formulations may be used to implement mechanized rearing processes of many beneficial insects that can not be produced economically by current methods.

Thus the present invention is directed in part to the use of lambda-carrageenan that acts as a solidifying agent to prepare artificial diet formulations for insects such as lepidopterans (e.g., cabbage looper, tobacco budworm), coleopterans (e.g., coffee berry borer) and mites (e.g., two-spotted spider mite and its predator persimilis), and which can be mixed at room temperature. The lambda carrageenan synergizes with starches, preferably corn starch, by producing a stable solid or semi-solid substrate which makes it unique for developing simplified insect diet formulations.

Generally, the insect diet formulation can contain the following (% weight):

| Ingredients | % low | % high |
| --- | --- | --- |
| Water | 43.2 | 85 |
| Protein | 1.44 | 5.7 |
| Carbohydrates | 2 | 16.99 |
| Cellulose fiber | 1.2 | 25.12 |
| Vitamins | 0.31 | 0.804 |

-continued

| Ingredients | % low | % high |
| --- | --- | --- |
| Salts | 0.75 | 1.16 |
| Sterols | 0.04 | 4.08 |
| Lipids | 0.98 | 4.68 |
| Preservatives | 0.048 | 1.44 |
| Lambda-carrageenan | 1.16 | 4.04 |
| Maltodextrin | 0.45 | 1.57 |

The insect diet formulation contains water such as Evian® natural spring water, drinking RO water, grade I RO water, and distilled water. Water concentration can be modified depending on the desired hardiness of the insect diet formulation; for example, about 49 to about 59% (e.g., 49-59%; preferably about 51 to about 53% (e.g., 51-53%) for solid diets, about 60 to about 69% (e.g., 60-69%; preferably about 60 to about 63% (e.g., 60-63%) for semisolid diets, and about 70 to about 89% (e.g., 70-89%; preferably about 83% (e.g., 83%) for semi liquid diets.

The composition contains proteins known to be beneficial to rearing insects, for example soy protein, soy flour, wheat germ, egg yolk, caseins, yeast, and others known in the art.

The composition contains carbohydrates (e.g., starch, cellulose, sugars) known to be beneficial to rearing insects. Sugars that can be used include, for example, glucose, fructose, maltose, sucrose, honey, and others known in the art. Starches that can be used include, for example, corn starch (e.g., starch, corn, food grade, Product NO, 3200, BioServ, Frenchtown, N.J.; corn starch powder, P. No. 39883, Bulkfoods.com, Toledo, Ohio; Argo®corn starch, Kroger, Greenville, Miss.) and potato starch powder (Manitoba starch Products, Rohtstein Corporation, www.manitobastarch.com, New England, New Jersey & Metro New York). Cellulose that can be used include, for example, cellulose fiber (powder, product No. 3425 BioServ, Frenchtown, N.J.), Alpha cel®, cellulose powder, naturally fibrous Solka-Floc®, JustFiber®, and NutraFiber® International Fiber Corporation, North Tonawanda, N.Y., Microcrystalline Cellulose Powder (MCCP), Alfacel-P food grade, Reliance Cellulose Products Ltd.www.reliance-cellulose.com, Japan.

The composition contains vitamins known to be beneficial to rearing insects, for example a vitamin premix (USDA vitamin premix) containing the following:

| Ingredient | Units/kg | Units |
| --- | --- | --- |
| Vitamin A | 22,000,000 | IU |
| Vitamin E | 7,999 | IU |
| Vitamin $B_{12}$ | 2.002 | Mg |
| Riboflavin | 499 | Mg |
| Niacinamide | 1,012 | Mg |
| d-Pantothenic Acid | 920 | Mg |
| (ca d-Pantothenate) | 1001 | Mg |
| Choline | 43,999 | Mg |
| (Choline Cl) | 49,999 | Mg |
| Folic Acid | 251 | Mg |
| Pyridoxine | 205 | Mg |
| (Pyridoxine HCl) | 251 | Mg |
| Thiamine | 222 | Mg |
| (ThiamineHCl) | 251 | Mg |
| d-Biotin | 20.2 | Mg |
| Inositol | 20,000 | Mg |
| Dextrose | (Add to 1 kg) | |

The composition also contains salts known to be beneficial to rearing insects. For example, salts that can be used in rearing lepidopterans:

| Wesson Salt Mixture, Product #F8680, BioServ | | |
|---|---|---|
| Ingredient | Amount (%) | Amount in 0.3 g |
| Calcium carbonate | 21 | 0.063 |
| Copper sulfate 5H$_2$O | 0.039 | 0.000117 |
| Ferric phosphate | 1.47 | 0.00441 |
| Manganese sulfate (anhydrous) | 0.02 | 0.00006 |
| Magnesium sulfate (anhydrous) | 9 | 0.027 |
| Potassium aluminum sulfate | 0.009 | 0.000027 |
| Potassium chloride | 12 | 0.036 |
| Potassium dihydrogen phosphate | 31 | 0.093 |
| Potassium iodide | 0.005 | 0.000015 |
| Sodium chloride | 10.5 | 0.0315 |
| Sodium fluoride | 0.057 | 0.000171 |
| Tricalcium phosphate | 14.9 | 0.0447 |
|  | 100 | 0.3 |

For example, salts that can be used in rearing spider mites and predatory mites:

| Chemical | | Amount for 100 ml Two spotted spider mite colloidal diet | Amount for 100 ml Persimilis colloidal diet |
|---|---|---|---|
|  | grams/100 ml salt A solution | | |
| Calcium chloride | 1.2 | 0.12 | 0.096 |
| Cobalt chloride 6H2O | 0.2 | 0.02 | 0.016 |
| Iron chloride 6H2O | 0.8 | 0.08 | 0.064 |
| Zinc chloride | 0.2 | 0.02 | 0.016 |
| d-water | 97.6 | 9.76 | 7.808 |
| total ml | 100 | 10 | 8 |
|  | grams/100 ml salt B solution | | |
| Potassium phosphate dibasic | 2.96 | 0.296 | 0.2368 |
| Sodium phosphate dibasic | 0.4 | 0.04 | 0.032 |
| d-water | 96.64 | 9.664 | 7.7312 |
| total ml | 100 | 10 | 8 |

For example, salts that can be used in rearing mites and Coffee berry borer:

| Evian ® natural spring water, Danone Co. Salt content | |
|---|---|
| Chemical | mgs 100 ml |
| Calcium | 7.800 |
| Chloride | 4.000 |
| Bicarbonate | 35.700 |
| Magnesium | 2.400 |
| Nitrate | 0.100 |
| Potassium | 0.075 |
| Sodium | 0.500 |
| Sulfates | 1.000 |
| Silica | 1.400 |

The composition can also contain preservatives, for example methyl paracept, sorbic acid, sorbic acid (potassium salt), ascorbic acid, propionic acid (phosphoric acid solution), sterptomycin sulfate, aureomycin sulfate, BHT, and others known in the art.

The composition contains lambda carrageenans. Carrageenans are polysulfated polysaccharides with polymers of repeating D-galactopyranose disaccharides (Glicksman, M., 1983, Food Hydrocolloids, Vol. 2: 73-113, CRC press, Inc. Boca Raton, Fla.). They are extracted from marine red algae (seaweeds) and used as food additives which are classified as "generally regarded as safe" (GRAS) by the Food and Drug Administration. Carrageenans are defined by the Food and Drug Administration according to their sources and usage and applications (CFR Title 21). Carrageenans are refined hydrocolloids extracted from the families of Gigartinaceae and Solieriacea of the class Rodophyceae (red seaweed); *Chondrus crispus, Chondrus ocelalatus, Euchema cottonii, Euchema spinosum, Gigartina acicularis, Gigartina pistillata, Gigartina radula* and *Gigartina stellata*. Other sources of carrageenans are *Gloiopeltis, Iridaea, Furcellaria fastigiata* (Belitz, H.-D., and Grosch, W. (1986), Carbohydrates IN: Food Chemistry, Springer Verlag, New York, N.Y., pp. 201-256), *Hypnea musciformis, Gigartina skottsbergii* (Rees, D. A., (1963), The carrageenan system of polysaccharides, part I the relation between the κ- and λ-components, London J. Chem. Soc., Part II: 1821-1832; Cerezo, (1967), London J. Chem. Soc. (C), 992). Carrageenans contain sulfated polysaccharide with dominant hexose of galactose and anhydrogalactose. Carrageenans contain sulfates in a range of 20-40% dry weight. Salts of carrageenans include ammonium, calcium, potassium or sodium salts. The structures, chemistry, functions, applications and food additive uses of carrageenans and polysulfated polygalactans are described by Picullell (Picullell, L. (1995), Gelling Carrageenan, IN: Food Polysaccharides and their applications, (A. M. Stephen, Editor), Marcel Dekker, Inc., pp. 205-244; Belitz, H.-D., and Grosch, W. (1986); Glicksman, M. (1983), *Food Hydrocolloids*, Vol. 2: 73-113, CRC press, Inc., Boca Raton Fla.; Rees, D. A. (1961), Estimation of the relative amounts of isomeric sulphate esters in some sulfated polysaccharides, London J. Chem. Soc., Part IV: 5168-5171; Rees, D. A. (1963); Guthrie, R. D., et al. (1968), Carbohydrate Sulphates, IN: Carbohydrate Chemistry, The Chemical Society Burlington House, London, pp. 254-269; Kroschwitz, J. E, et al., Eds. (1994), Encyclopedia of Gum Technology, Volume 12, John Wiley and Sons, New York, N.Y.; Dea, I. C. M. (1982), Polysaccharide conformation in solutions and gels, IN: Food Carbohydrates (D. R. Lineback and G. E. Inglett, Editors), Avi Publishing Co., Westport Conn., pp. 420-457).

An example of a lambda carrageenan which can be utilized in the present invention is CSW-750 sold by TIC GUMS (Belcamp, MD) and which contains carrageenan and maltodextrin, CAS #9000-07-1, 9050-36-6 (maltodextrin), and contains per 100 g: sodium (6775 mg), potassium (1054 mg), calcium (220 mg), soluble dietary fiber (60 g), insoluble dietary fiber (7 g), and protein (1 g). Another example of lambda carrageenan is Fluka product No. 22049, Sigma-Aldrich-Fluka, St. Louis, Mo., which can be used with Dextrin 5 (maltodextrin), Fluka product No. 51636, Sigma-Aldrich-Fluka The composition can also contain sterols, for example cholesterol, ergosterol, beta sitosterol, campesterol, stigmasterol, or others known in the art.

The composition can also contain lipids, for example oil of the following: canola, olive, corn, peanut, soy bean, cotton, flax, soy lecithine, fish, salmon, or others known in the art.

The new insect diet formulations can be prepared, for example, by mixing 2-4% by weight CSW-750 (sold by TIC GUMS) with the dry components of the arthropod diet (e.g., proteins, salts, vitamins, carbohydrates, preservatives) and then adding 50-60% by weight distilled or Evian® drinking water at room temperature and homogenizing the mixture to a smooth texture. Water concentration can be modified depending on the desired hardiness of the insect or mite diet formulation; for example, about 51 to about 53% for solid diets and about 60% for semisolid diets and 67% for semisolid diets. The mixing container with the insect diet formulation is then covered and left to rest at room temperature for about 20 min.

Other known components of artificial insect diet formulations may be added.

The unique properties of the diet formulation allow feeding by arthropods with different types of mouth parts. Insects with mandibles can easily chew it and ingest it as diets based on agar; however, in contrast to agar, the diet formulation of the present invention will also allow feeding by arthropods with piercing or sucking mouth parts because liquid compounds of the diet are in suspension and readily available for external digestion and ingestion. Mites process food by external digestion injecting enzymes through their chelicerae and sucking the liquid products of digestion through their mouth parts. This has limited existing artificial diets for mites to liquid formulations. Unfortunately, liquid formulations reduce the efficiency of the external digestion process making these diets marginal at best. The use of the diet formulation of the present invention provides an excellent substrate for external digestion allowing a more efficient use of the available nutrients. For example, six g of the diet can be weighed out into 20 ml glass vials or plastic trays to rear lepidopterans and coleopterans, and 1 ml can be dispensed on top of a stretched Parafilm® sheet and sandwiched to form a protective barrier by sealing the edges with a roller to rear mites.

The formulations can also be heated if required for the diet formulation. Formulated diets can be stored in the refrigerator at 4° C. in the dry form for several months or for 5 days at 4° C. if already formulated or in the freezer for at least a month. Diet formulations stored for a long time may lose their physical characteristics due to the loss of water by desiccation. The diet formulation can be restored to its original characteristics by adding water and remixing.

The presence of salts in the diet formulation are for nutritional purpose only. It is the presence of cellulose in the formulation and the addition of starch (e.g., 6%) which provide extra strength and stability of the solid diets. Furthermore, the addition of antioxidants improved the stability of the semi-solid diets. Evaluation of first generation of insects and mites reared on these diets showed no significant differences on developmental time, survival, or fecundity when compared to agar diets for lepidopterans and coleopterans, and lima bean leaves or prey for mites.

Furthermore, the diet formulation is 100% water soluble, which eliminates disposal problems. The diet formulation is a unique, innovative, easy to prepare, effective, affordable, and environmentally friendly process to rear insects and mites. The use of a gelling agent that does not require heating (in contrast to agar) simplifies the formulation of solid and semi-solid artificial diets. Furthermore, critical nutritional components can be mixed in one step without risk of thermal degradation. These diet formulations can be adjusted to resemble more closely the natural host, nutritionally as well as physically, and as a consequence the produced insects are healthier, thereby providing a better host to produce beneficial organisms (parasite, microbes, etc.). By eliminating agar from the diet formula, the mechanized process of mass insect propagation can be greatly simplified through the elimination of heating and temperature control required during the dispensing process and the cooling required for the safe planting of eggs on the insect diet formulation.

Solid insect diets formulations of the present invention are much simpler to prepare. By eliminating the need for high temperatures during the mixing process, the nutritional quality of the diet formulation is never compromised during the diet preparation process. This provides a more consistent nutritional value of the diet formulation resulting in the production of insects of better quality. Mechanized insect production using an agar-based diet formulation is a very expensive process because it requires strict temperature control for the mixing and dispensing of the diet. After the diet has been dispensed in containers it must be cooled down below 30° C. before insect eggs can be safely planted on the diet. Insect eggs are highly sensitive to high temperatures, which can kill the eggs or reduce the hatching percentage. The mechanization of insect production using the diet formulation of the present invention can be simplified by eliminating temperature control and dispensing of liquids. This diet formulation can be extruded into any type of container including plastic bags eliminating the need of complex dispensing equipment. Because these formulations can be mix at room temperature, there is no need for temperature control or cooling processes and no risks of nutrient thermal breakdown or loss of egg viability. Because lambda carrageenan is considerably cheaper than agar, the cost of mass producing insects and mites for different applications can be reduced significantly. This may reduce the cost of mass production of biological control agents making the practice of biological control more competitive to standard (less environmentally friendly) pest control practices. As a consequence, it may be possible to mass produce more species of natural insect enemies economically, making some arthropod pests amenable to biological control for the first time.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Example 1

Evaluation of Diets to Rear Cabbage Looper, *Trichoplusia ni* (Lepidoptera: Noctuidae)

A commercially available agar-based formulation produced by BioServ was prepared by weighing out 14.4 g Lepidoptera diet mix (Product No. 7060, Bio-Serv) and transferring it to a 200 ml glass beaker, adding 30 ml room temperature distilled water, mixing with a spatula and the set aside. In a 100 ml glass beaker, 1.70 g agar was weighed out and mixed with 40 ml distilled water, this was brought to a boil in a microwave until foamy (2 minutes at high power), stirred occasionally and repeated 2 more times, 16 ml of room temperature distilled water was added and mixed. This was poured slowly into the Lepidoptera diet mix while stirring with a plastic spatula and mixed well. 8 ml were poured into 20 ml glass vials.

Colloidal diet preparation: Dry ingredients (Table 1) were weighed out and placed into a 200 ml glass beaker and mixed well. Water was added and incorporated until the mixture was homogeneous. The beaker was covered with foil and left to sit for 20 min at room temperature. 6 g were weighed out and placed into 20 ml glass vials.

Using a number 2 surface sterilized (200 proof ethanol) brush, two first instar larvae were introduced into each of 50 vials and the vials were plugged with a cotton ball. The vials were placed upside down in a plastic container covered with a lid to prevent first instars from moving away from the diet following their natural negative geotropism. Vials were incubated in a Percival environmental chamber at 28±1° C., 67 RH, and 16:8 (L:D) h photoperiod. Fifty 20-ml glass vials were prepared for each of the diet formulations. Each vial was filled with 8 ml of diet. Two first instars *T. ni* were introduced to each vial and allowed to complete development at the conditions described above. Development time from first instar to adult, pupal weight, and survival were recorded. *T. ni* adult fecundity and survival were determined by placing 20 newly emerged pairs of male and female adult moths into a 125 ml glass Erlenmeyer flasks. A cotton ball soaked with 10% sucrose was provided as food source and a strip of paper towel was inserted in the flasks to provide a surface for oviposition. The mouths of the flasks were covered with a piece of paper towel and secured with a rubber band. Every 3 days the surviving moths were transferred to clean flasks and eggs on the surfaces of the flasks and paper strip were counted under a stereo microscope.

Developmental time of *T. ni* was significantly longer (20.47±0.08 d) when feeding on the colloidal diet as compared to *T. ni* feeding on the agar-based diet (19.73±0.077 d) (F=42.97; df=1, 141; P<0.0001). However, pupal weight was not significantly different between *T. ni* developing on the colloidal diet (214.35±3.91 mg) and those that developed on the agar-based diet (215.09±3.72 mg). No significant differences were found on female fecundity either. Females that completed development in the colloidal diet oviposited a mean of 746.6±99.3 eggs while females completing development in the agar-based diet oviposited a mean of 682.3±99.3 eggs. Survival from first instar to adult was 67% in the colloidal diet and 74% in the agar-based diet. The net reproductive rate of *T. ni* developing on colloidal diet was 250.11 female eggs per female which was not significantly different to *T. ni* developing on agar-based diet (252.45 female eggs per female).

Without being bound by theory, because the *T. ni* used in this evaluation has been reared in agar-based diet for more than 100 generations, it was expected to observe some differences when the diet formulation was changed. After 5 generations of rearing in the colloidal formulation, *T. ni* mean larval developmental time had been reduced by 1 day. This effect is due to a common phenomenon observed in some species of Lepidoptera exhibiting behavioral plasticity on feeding preferences of different plant species (Hanson, F. E., The behavioral and neurophysiological basis of food plant selection by lepidopterous larvae, pp. 3-23, In Ahmad, S. [Ed.], Herbivorous insects: host-seeking behavior and mechanisms, 1983, Academic Press, New York, N.Y.). The first generation invading a new suitable plant species goes through a process of conditioning. The following generations steadily change their feeding preferences towards the new plant species. This same phenomenon is observed when lepidopterans reared in artificial diets are transferred to a new diet formulation.

The colony of *T. ni* was continuously reared in the colloidal diet formulation for 10 generations under the same conditions above described. The F 10 was then evaluated using the same methods described above and the data was compared to that obtained for the F1 colloidal diet and the BioSery diet.

Figure 2:
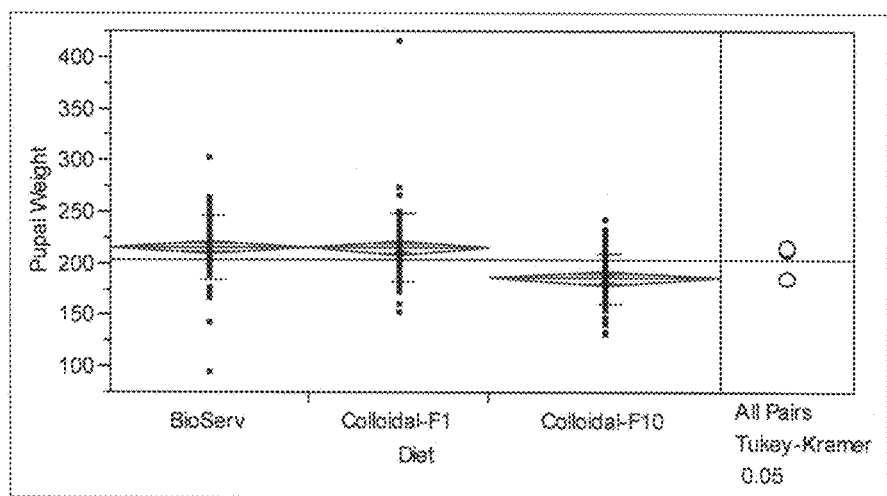
FIG. 2 shows analysis of variance and mean comparison of pupal weight in mg among $T.$ $ni$ reared on colloidal diet for one and 10 generations and in the BioServdiet. Rhombs middle line represents means, rhomb height represents confidence intervals, rhomb width represent number of observations and points represent observation values. Circles represent results of the Tuke-Kramer HSD test, overlapping circles correspond to means that are not significantly different.
Figure 3:
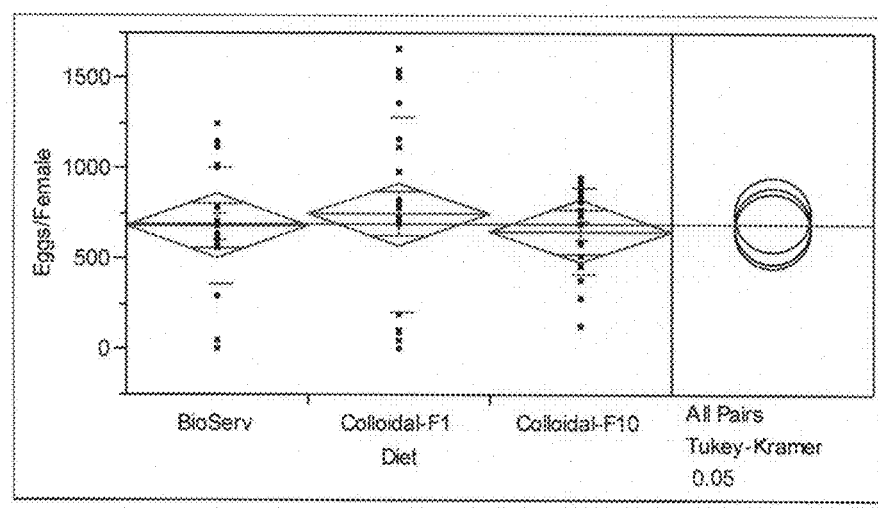
FIG. 3 shows analysis of variance and mean comparison of total number of eggs per female among $T.$ $ni$ reared on colloidal diet for one and 10 generations and in the BioSery diet. Rhombs middle line represents means, rhomb height represents confidence intervals, rhomb width represent number of observations and points represent observation values. Circles represent results of the Tuke-Kramer HSD test, overlapping circles correspond to means that are not significantly different.

After 10 generations in the colloidal diet the development time significantly decreased to 15.13 days. This developmental time was significantly shorter than that observed for *T. ni* developing on the BioSery diet (F=2090.8; df=2, 227; P<0.0001) (FIG. 1). Pupal weight significantly decreased after 10 generations in the colloidal diet. The pupal weight of *T. ni* was significantly lower in the colloidal diet F10 (185.1±23.9) as compared to the colloidal diet F1 and the BioSery diet (214.3±33.2 and 215.1±31.5, respectively) (F=27.5; df=2, 227; P<0.0001) (FIG. 2). Despite of the significant reduction observed in pupal weight, fecundity was not significantly impacted after 10 generations in the colloidal diet. Total number of eggs per female was not significantly different among the 3 treatments (FIG. 3).

Example 2

Evaluation of Diets to Rear Tobacco Budworm *Helicoverpa virescens* (Lepidoptera: Noctuidae)

An experiment similar to Example 1 was performed for the tobacco bud worm, *Helicoverpa virescens* (Lepidoptera: Noctuidae). The colloidal diet formulation from Table 1 was compared to the agar-based USDA Lepidoptera diet formulation following the same directions as above using 13.2 g in 14 ml d-water, 2.13 g agar in 45 ml, then 26 ml cold water. Once agar solution and diet mixture was homogeneous, 0.250 ml of propionic: phosphoric acid (41.8%:4.2%) was added. Preparation of *H. virescens* colloidal formulation was done following the same directions as for *T. ni* using *H. virescens* diet formulation (Table 1).

Fifty 20-ml glass vials were filled with 8 ml of each of the 2 diet formulations. Two first instar larvae were added to each vial and the vials were incubated until the larvae completed development under the same conditions described above.

Comparison of developmental time and pupal weight of *H. virescens* developing on colloidal diet versus agar-base diet formulations showed significant differences. Developmental time was more than 2 days longer in *H. virescens* developing on the colloidal formulation (16.75 days versus 14.0 days) and this difference was statistically significant (F=441.69; df=1, 92, P<0.0001). Pupal weight was 230.21±5.3 mg in the colloidal diet versus 328.04±5.41 mg in the agar-based diet and this difference was statistically significant (F=166.76; df=1, 92; P<0.0001). Comparison of F3 H. virescens developing on colloidal diet still showed a significantly longer developmental time; however, pupal weight improved to 319.34±4.87 mg and this was no longer significantly different than weights obtained from agar-based diet rearing.

Example 3

Evaluation of Diets to Rear Coffee Berry Borer, *Hypothenemus hampei* (Coleoptera: Scolytidae)

The agar-based formulation used is presented in table 2. The main ingredients (coffee meal, soy bean flour, sugar, ethanol, agar, lecithin, ergosterol, and sorbic acid) were weighed out and placed into a 500 ml autoclavable plastic squeeze bottle, water was added and mixed well, and sterilized on liquid cycle at 2.9 KPa of pressure for 15 min. A water bath at 45° C. was set under a laminar flow hood. After sterilization the bottle with the diet was placed in the bath and left to cool to 47° C. USDA vitamin mixture (Vitamin Premix) and streptomycin sulfate was added and mixed well by hand shaking. 2 ml diet was poured into 10 ml sterile glass vial and left to sit until the diet reached room temperature. Using a surface sterilized paint brush No. 2, five *H. hampei* adults were placed in each of 50 vials and plugged with a sterile cotton plug. The vials were placed into a plastic box and incubated in a Percival environmental chamber under dark conditions at 27±1° C. and 70% RH. The data generated from this experiment was compared to data obtained from a similar experiment using colloidal diet (described below). The environmental conditions were replicated accurately, but only 16 repetitions were done due to the lack of a mother colony. Coffee berry borers were provided by USDA ARS, SPCL, Beltsville, Md. and had been reared on an agar based diet.

The colloidal formulation was prepared by weighing out main ingredients (coffee meal, soy bean flour, sugar, ethanol, lecithin, and ergosterol, but no agar) into a 200 ml glass beaker, water was added and mixed well, the beaker was covered with foil and autoclaved at 2.9 KPa of pressure for 15 min. After sterilization, the mix was allowed to cool down to room temperature, the rest of the ingredients (e.g., vitamins, preservatives, yeast, maltodextrin and lambda carrageenan) was added and mixed well with a spatula. The beaker was covered with foil and left to sit for 20 minutes. 6 g diet was transferred into each of sixteen 25 ml sterile glass Scintillation vials and inoculated as above, and the vials were capped tight enough to allow minimal amount of air exchange, and incubated as above. If the diet dried out, 100 μl sterile distilled water was added using a sterile syringe. Evaluations were done by counting under a stereo-microscope the number of eggs, larvae, and adults after 2 months of diet infestation.

Data collected for *H. hampei* showed that these insect started to lay eggs after 2 weeks of being transferred to fresh agar diet, and that a mean yield of 5 fold was obtained after 2 months (data not shown). Similarly, beetles reared in the agar diet and transferred to the colloidal diet started laying eggs after 2 weeks which indicated that the colloidal diet did not have an adverse effect on adults. The first generation of adults occurred 2 months after infestation. The population count on the 16 vials was a total of 251 adults, 161 larvae, and 838 eggs. Compared to data collected from the agar-based diet, the colloidal diet produced significantly lower number of adults per vial (15.69 compared to 25.68; F=348.42; df=1, 64; P<0.0001), larger number of pupae (10.06 compared to 7.34; F=88.84; df=1, 64; P=0.0024), and smaller population growth (5.15 fold compared to 6.6 fold; F=52.70; df=1, 64; P<0.0001). This indicated that the colloidal formulation was still of slightly lower quality than the agar-based formulation. However, a coffee berry borer colony was maintained for at least 5 generations with the colloidal diet without detrimental effects.

Example 4

Evaluation of Diets to Rear Two-Spotted Spider Mite (*Tetranychus urticae*) (Prostigmata: Tetranychidae)

Ingredients for the colloidal formulation (Table 3) were measured out and combined with water and sorbic acid in a 150 ml glass beaker, salts solutions A and B (described above) were added in sequential order, and the beaker set aside. Lecithin, ergosterol, flax oil, and plant powder were weighed out and placed into a 25 ml glass beaker, lauryl sulfate was added and mixed, and left to sit at room temperature while the rest of the diet was prepared. The rest of the dry ingredients (carbohydrates, proteins, vitamins, and lambda carrageenan (table 3)) were weighed out and placed in a second 150 ml glass beaker. The lauryl sulfate mix was added to the water solution and mixed well and then added to the dry ingredients and mixed well using a spatula. The beaker was covered with foil and left to sit at room temperature for 10 min. 4×4 cm pieces of Parafilm® were cut and stretched on all its sides to obtain an area twice its original size. 1 ml colloidal formulation was placed on one side of the stretched Parafilm® and sandwiched it with the other end and sealed by folding the edges and securing them with a roller.

Pieces of sandwiched diet were placed into a 50 ml plastic container (previously modified with 2, opposite 1 cm diameter holes covered with a screen, to allow air circulation) containing 20 spider mite eggs. The eggs were incubated at 27±1° C., 60% RH, and 14:10 (L: D) h photoperiod. Developing mites were provided with fresh diet every 3 days. The control group consisted of an equal number of spider mite eggs placed on Lima bean (Phaseolus lunatus) leaves and maintained at the same environmental conditions. Fresh leaves were provided as needed. The experiment was repeated 16 times. Adults were counted under a stereo-microscope at the end of 5 days after the hatching of the eggs.

Survival of mites from egg to adult in the bean leaves was 97.5%. Survival in the colloidal diet was 80.31%. This difference was significant after performing Z-test (Z=6.697, df=319, P<0.0001). Spider mites were successfully reared in this artificial diet formulation for more than 10 generations.

Table 4 shows range of content in percentage of basic nutrients of the colloidal diet for lepidopterans showing the optimal composition and lower and upper ranges for each of the nutrients and the colloid substrate.

Example 5

Evaluation of Diets to Rear Predatory Mite (*Phytoseiulus persimilis*) (Mesostigmata: Phytoseiidae)

The formulation was prepared and used following the same instructions as above for the spider mite diet mixing using ingredients listed in Table 3. Ten predatory mites per repetition were used. Control was spider mite infested lima bean and 10 predatory eggs were allowed to be laid. After that adults were removed. Treatment and control were incubated in a Percival environmental chamber at 28±1° C., 16:8 (L: D)

h photoperiod, and 70% RH. The experiment was repeated 16 times. Adults were counted under a stereo-microscope 5 days after the hatching of the egg.

Survival from egg to adult was higher in mites which developed on the natural prey (93.75%) compared to those that developed on the colloidal artificial diet (83.75%). These differences were significant after performing Z-test (Z=2.658, df=159, P=0.008). This survival value in artificial diet was good enough to justify it use for mass production of P. persimilis, and this artificial diet formulation may be useful to maintain predatory mites healthy during storage and transport.

Example 6

Comparison of Diets to Rear Western Tarnish Plant Bugs, *Lygus hesperus* Knight (Hemiptera: Miridae)

The colloidal diet formulation from Table 5 was compared to NI *Lygus* diet (Cohen 2000) (Table 6) currently used at USDA ARS NBCL.

Preparation of *L. hesperus* colloidal formulation: The preparation of the colloidal diet for *L. hesperus* was done following the same directions as for preparation of the two-spotted spider mite and predatory mite diet formulations. Honey was mixed with the water previously to be incorporated to the rest of the ingredients. Lima bean meal, toasted wheat germ and RO water were placed inside of an 80 ml glass beaker and mixed with a Teflon spatula. The beaker was covered with foil and autoclaved (wet cycle) at 1.4 kg/cm$^2$ for 15 min. The mixture was allowed to cool to room temperature and mixed with the rest of the ingredients (Table 5) using a blender. Three g of diet was placed between slightly stretched Parafilm sheets as it was done for the spider mite diet and presented to the nymphs thru a polyester screen.

Cohen's NI diet preparation: Component A: Water, sucrose and honey were placed into a 50 ml glass beaker on top of a hot until boil. Then, the acetic acid solution and brewer's yeast were added and the mix was brought to a rapid rolling boil. Eggs (previously blended) were added. The mix was stirred until consistency of scramble eggs. The beaker was removed from hot plate and allowed to cool down at room temperature. Component B: Dry ingredients were mixed into a 400 ml glass; water and previously blended egg yolk were added and mixed with a spatula. The beaker was covered with foil and autoclaved at 1.4 kg/cm$^2$ for 20 min. Beaker was removed from autoclave and allowed to cool down to 50° C. Component C: Ingredients were placed into a Warning blender. Components A and B were added and blended for 2 minutes at low speed. Mixture was shaken for a minute and blended again for 1 minute at high speed. 3 g diet was transferred with a stainless steel spatula into Parafilm bags to make food pouches. The pouches were sealed with a roller and kept refrigerated at 8° C. for 1 week.

Comparison of the 2 diets: *Lygus hesperus* specimens used for the comparisons were reared on NI (Cohen, 2000) diet for more than 100 generations. The mother colony is maintained in the facilities of the USDA-ARS National Biological control Laboratory at Stoneville, Miss. *Lygus* first instars for Colloidal F1 and Ni diet treatments were obtained from eggs oviposited inside gelcarin packets maintained at 27° C. and 67% RH. Twenty groups of twenty first instars each were obtained from the mother colony by transferring the first instars with the help of a soft bristle, No. 0 brush to 125 ml round plastic containers filled with shredded paper. The containers (one per group) were tightly closed with their lids, to which a big hole in the middle was previously cut to allow the insect to feed thru a polyester screen. Ten groups were provided with pouches containing Cohen's NI diet and the other 10 with pouches containing the colloidal diet formulation. Diet pouches were placed on top of the rearing containers' screen cover, which allowed the nymphs to feed through the openings. All 20 groups were also provided with a Petri dish cover (40 mm diameter) containing a 50% mixture of polyacrylamide polymer (T-400) and distilled water covered by a Parafilm sheet. The dishes were placed on top of the rearing containers' screen cover with the Parafilm sheet in contact with the screen. Dishes provided water for all developing stages and oviposition sites for adult females.

All containers were kept at 27±1° C., 65±5% RH, and 14:10 h (LL:DD) photoperiod. Oviposition dishes with eggs were replaced daily and the number of eggs oviposited were counted and recorded daily until all individuals in the group died. The number of adult females completing development in each group was used to estimate total number of eggs oviposited per female. Proportion of viable eggs was easily determined by observation under microscope. Unviable eggs appear clear colored and viable eggs presented a pearly white coloration. The red colored eyes of developing first instars were observed in the interior of viable eggs of 3 days or older but not in unviable ones at the same age. Proportion of viable eggs was calculated by dividing total number of viable eggs per female by total number of eggs oviposited per female.

At the end of this experiment, first instars from the groups reared with the colloidal diet were maintained in similar containers and were reared for 5 generations under the same environmental conditions described above. The F5 generation reared in the colloidal diet was then evaluated using the same method described above. *Lygus* first instar nymphs from colloidal colony F5 were obtained from eggs laid inside a Petri dish containing a 50% mixture of polymer (T-400) and distilled water, lined with unstreached Parafilm.

Figure 4:
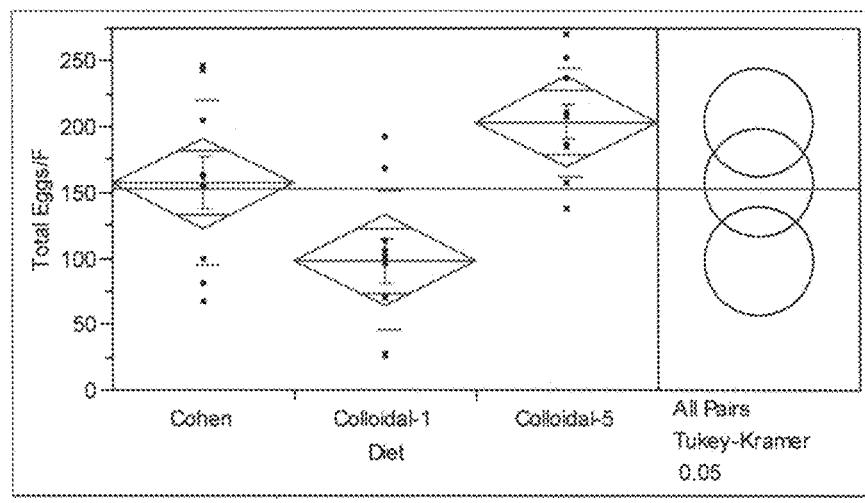
FIG. 4 shows analysis of variance and mean comparison of total number of eggs per female among groups of $L.$ $hesperus$ reared on colloidal diet for one and 5 generations and in the NI (Cohen 2000) diet (Cohen, A. C., J. Entomol. Sci. 35(3): 301-310 (2000)). Rhombs middle line represents means, height represents confidence intervals and points represent observation values. Circles represent results of the Tuke-Kramer HSD test, overlapping circles correspond to means that are not significantly different.
Figure 5:
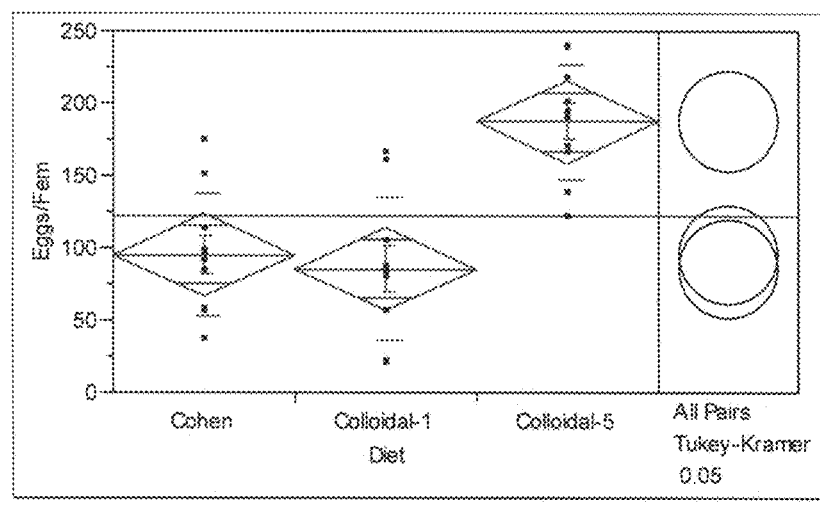
FIG. 5 shows analysis of variance and mean comparison of number of viable eggs per female among groups of $L.$ $hesperus$ reared on colloidal diet for one and 5 generations and in the NI (Cohen 2000) diet. Rhombs middle line represents means, height represents confidence intervals and points represent observation values. Circles represent results of the Tuke-Kramer HSD test, overlapping circles correspond to means that are not significantly different.

Evaluation results: The total number of eggs oviposited per female was significantly lower in the F1 generation reared on colloidal diet than in the F5 reared in colloidal diet and the control reared in the NI diet (F=10.09; df=2, 27; P=0.0005) (FIG. 4). No difference in total number of eggs per female was observed between the colloidal diet F5 and the control diet NI. However, the proportion of eggs that were viable was significantly higher in both colloidal diet treatments (0.865 and 0.919 for F1 and F5, respectively) than in the control diet NI (0.595) (Z=34.92 and 66.83; df=15,668 and 29,403, respectively P<0.0001 for both). This resulted in a significantly higher number of viable eggs per female in the F5 generation in colloidal diet as compared to the F1 colloidal diet and the control diet (F=16.29; df=2, 27; P<0.0001) (FIG. 5). The number of viable eggs produced per female was not significantly different between groups feeding on colloidal diet F1 and control NI diet. Eggs oviposited by females reared in the NI diet hatched in 5 to 6 days, while eggs oviposited by females reared in the colloidal diet hatched in 3.5 to 4.5 days at 27° C. There was no significant difference in development time from first instar to adult among the 3 treatments; however, immature survival was significantly lower in the first generation developing on the colloidal diet (Z=12.6 and 13.0; df=1321 and 1436; P<0.0001, for Cohen's and colloidal F5, respectively). Immature survival of the fifth generation developing on colloidal diet was not significantly different from that observed on the Cohen's NI diet. Individuals of *L. hesperus* grown on Cohen's NI diet were noticeably more fragile to the touch than individuals grown on the colloidal diet.

Oneway Analysis of Total Eggs/F By Diet
Oneway Anova
Analysis of Variance

| Source | DF | Sum of Squares | Mean Square | F Ratio | Prob > F |
|---|---|---|---|---|---|
| Diet | 2 | 56045.67 | 28022.8 | 10.0933 | 0.0005 |
| Error | 27 | 74961.94 | 2776.4 | | |
| C. Total | 29 | 131007.61 | | | |

Means and Std Deviations

| Level | Number | Mean | Std Dev | Std Err Mean | Lower 95% | Upper 95% |
|---|---|---|---|---|---|---|
| Cohen | 10 | 157.084 | 62.1992 | 19.669 | 112.59 | 201.58 |
| Colloidal-1 | 10 | 98.039 | 52.7513 | 16.681 | 60.30 | 135.78 |
| Colloidal-5 | 10 | 203.668 | 40.9594 | 12.952 | 174.37 | 232.97 |

Means Comparisons
Comparisons for all pairs using Tukey-Kramer HSD

| q* | | Alpha |
|---|---|---|
| 2.47942 | | 0.05 |
| Level | | Mean |
| Colloidal-5 | A | 203.66760 |
| Cohen | A | 157.08444 |
| Colloidal-1 | B | 98.03917 |

Levels not connected by same letter are significantly different.

Oneway Analysis of Viable Eggs/Fem By Diet
Oneway Anova
Analysis of Variance

| Source | DF | Sum of Squares | Mean Square | F Ratio | Prob >F |
|---|---|---|---|---|---|
| Diet | 2 | 63026.72 | 31513.4 | 16.2924 | <.0001 |
| Error | 27 | 52224.37 | 1934.2 | | |
| C. Total | 29 | 115251.09 | | | |

Means and Std Deviations

| Level | Number | Mean | Std Dev | Std Err Mean | Lower 95% | Upper 95% |
|---|---|---|---|---|---|---|
| Cohen | 10 | 95.019 | 42.6054 | 13.473 | 64.54 | 125.50 |
| Colloidal-1 | 10 | 85.351 | 49.2530 | 15.575 | 50.12 | 120.58 |
| Colloidal-5 | 10 | 187.056 | 39.5175 | 12.497 | 158.79 | 215.32 |

Means Comparisons
Comparisons for all pairs using Tukey-Kramer HSD

| q* | | Alpha |
|---|---|---|
| 2.47942 | | 0.05 |
| Level | | Mean |
| Colloidal-5 | A | 187.05556 |
| Cohen | B | 95.01889 |
| Colloidal-1 | B | 85.35107 |

In summary, the colloidal diets presented in this report were of sufficient quality to justify further development. While in many cases the quality of the resulting arthropods was reduced, the magnitude of the reduction is such that it may be eliminated after small modifications or after adaptation of the arthropods to the new formulation. Eliminating agar from the formulations reduces substantially the cost of the formulations and simplifies considerably the preparation process making them more suitable for mechanization.

All of the references cited herein, including U.S. Patents, are incorporated by reference in their entirety. Also incorporated by reference in their entirety are the following references: Cohen, A. C., Ann. Rev. Entomol., 40: 85-103 (1995)); Cohen, A. C., Am. Entomol., 44: 103-117 (1998); Hanson, F. E., The behavioral and neurophysiological basis of food plant selection by lepidopterous larvae, pp. 3-23, In Ahmad, S. [Ed.], Herbivorous insects: host-seeking behavior and mechanisms, 1983, Academic Press, New York, N.Y.

Thus, in view of the above, the present invention concerns (in part) the following:

A composition comprising (or consisting essentially of or consisting of) proteins, carbohydrates, vitamins, salts, and lambda carrageenan; wherein said composition contains maltodextrin and said composition contains no agar.

The above composition, wherein said composition contains preservatives.

The above composition, wherein said composition contains starch and cellulose.

The above composition, wherein said composition contains about 1.44-5.7 wt. % protein, about 2-16.99 wt. % carbohydrates, about 1.2-25.12 wt. % cellulose, about 0.31-0.804 wt. % vitamins, about 0.75-1.16 salts, about 0.04-4.08 wt. % sterols, about 0.98-4.68 wt. % lipids, about 0.048-1.44 wt. % preservatives, about 1.16-4.04 wt. % lambda carrageenan, and about 0.45-1.57 wt. % maltodextrin.

An insect diet formulation, comprising (or consisting essentially of or consisting of) the composition according to claim 1 and water.

The above insect diet formulation, wherein said water is room temperature water.

The above insect diet formulation, wherein said formulation contains about 43.2-85 wt. % water, about 1.44-5.7 wt. % protein, about 2-16.99 wt. % carbohydrates, about 1.2-25.12 wt. % cellulose, about 0.31-0.804 wt. % vitamins, about 0.75-1.16 salts, about 0.04-4.08 wt. % sterols, about 0.98-4.68 wt. % lipids, about 0.048-1.44 wt. % preservatives, about 1.16-4.04 wt. % lambda carrageenan, and about 0.45-1.57 wt. % maltodextrin.

The above insect diet formulation, wherein said formulation contains about 49 to about 59% water.

The above insect diet formulation, wherein said formulation contains about 60 to about 69% water.

The above insect diet formulation, wherein said formulation contains about 70 to about 89% water.

A method for rearing insects from eggs, said method comprising (or consisting essentially of or consisting of) providing the insect diet formulation according to claim 5 and culturing said insects with said insect diet formulation.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A method for rearing insects or mites from eggs comprising: providing to an insect or mite a solid or semi-solid or semi-liquid colloid diet formulation which comprises lambda carrageenan, starch, cellulose, maltodextrin, and water in amounts effective to produce a stable solid or semi-solid or semi-liquid colloid diet formulation for insects and mites which feed by chewing, piercing, sucking, and/or using external digestion, wherein said colloid diet formulation further includes proteins, carbohydrates, salts, and vitamins.

2. The method of claim 1 wherein said lambda carrageenan is present in a range of approximately 1.16 to approximately 4.04 percent by weight to produce a stable solid or semi-solid or semi-liquid colloid diet formulation.

3. An insect or mite rearing colloid diet formulation comprising an solid or semisolid or semi-liquid colloid formulation containing lambda carrageenan, starch, cellulose, maltodextrin, and water in amounts effective to produce a stable solid or semi-solid or semi-liquid colloid formulation for insects and mites which feed by chewing, piercing, sucking, and/or using external digestion, wherein said diet formulation is mixed with proteins, carbohydrates, salts, and vitamins wherein said colloid formulation does not require heat in its preparation.

4. The composition of claim 3 wherein said lambda carrageenan is present in a range of approximately 1.16 to approximately 4.04 percent by weight to produce a stable solid or semi-solid or semi-liquid colloid formulation.

5. An insect or mite rearing diet formulation for insects and mites which feed by chewing, piercing, sucking, and/or using external digestion, said diet formulation comprising proteins, carbohydrates, salts, vitamins, and water wherein said diet formulation is contained in a stable solid, semi-solid, or semi-liquid colloid comprising lambda carrageenan, starch, cellulose, maltodextrin, and water in amounts effective to produce a stable solid, semi-solid, or semi-liquid colloid, and wherein said stable solid, semi-solid, or semi-liquid colloid does not require heat in its preparation.

6. The diet formulation of claim 5 wherein said lambda carrageenan is present in a range of approximately 1.16 to approximately 4.04 percent by weight.

\* \* \* \* \*